(12) United States Patent
Whayne et al.

(10) Patent No.: US 6,972,023 B2
(45) Date of Patent: Dec. 6, 2005

(54) DISTAL ANASTOMOSIS SYSTEM

(75) Inventors: James G. Whayne, Chapel Hill, NC (US); Alexander Q. Tilson, Burlingame, CA (US); Sidney D. Fleischman, Menlo Park, CA (US); Charles S. Love, Santa Barbara, CA (US)

(73) Assignee: Converge Medical, Inc., Sunnyvale, CA (US)

(*) Notice: Subject to any disclaimer, the term of this patent is extended or adjusted under 35 U.S.C. 154(b) by 448 days.

(21) Appl. No.: 10/122,075

(22) Filed: Apr. 11, 2002

(65) Prior Publication Data

US 2003/0093095 A1 May 15, 2003

Related U.S. Application Data

(63) Continuation-in-part of application No. 09/899,346, filed on Jul. 5, 2001, now Pat. No. 6,626,920.
(60) Provisional application No. 60/333,276, filed on Nov. 14, 2001.

(51) Int. Cl.[7] ............................................. A61B 17/08
(52) U.S. Cl. ..................................... 606/153; 606/151
(58) Field of Search ............................... 606/151, 153, 606/155, 215

(56) References Cited

U.S. PATENT DOCUMENTS

| | | |
|---|---|---|
| 4,214,587 A | 7/1980 | Sakura, Jr. |
| 4,366,819 A | 1/1983 | Kaster |
| 4,368,736 A | 1/1983 | Kaster |
| 4,607,637 A | 8/1986 | Berggren et al. |
| 4,624,257 A | 11/1986 | Berggren et al. |
| 4,657,019 A | 4/1987 | Walsh et al. |
| 4,665,906 A | 5/1987 | Jervis |
| 4,787,386 A | 11/1988 | Walsh et al. |
| 4,917,087 A | 4/1990 | Walsh et al. |
| 4,917,090 A | 4/1990 | Berggren et al. |
| 4,917,091 A | 4/1990 | Berggren et al. |
| 4,950,227 A | 8/1990 | Savin et al. |
| 5,067,957 A | 11/1991 | Jervis |
| 5,078,736 A | 1/1992 | Behl |
| 5,156,613 A | 10/1992 | Sawyer |
| 5,190,546 A | 3/1993 | Jervis |
| 5,234,447 A | 8/1993 | Kaster et al. |

(Continued)

FOREIGN PATENT DOCUMENTS

EP      0 824 901      2/1998

(Continued)

OTHER PUBLICATIONS

U.S. Appl. No. 60/333,276, filed Nov. 14, 2001, Whayne et al.

(Continued)

Primary Examiner—Julian W. Woo
(74) Attorney, Agent, or Firm—Carol M. LaSalle; Bozicevic, Field & Francis LLP

(57) ABSTRACT

Distal anastomosis devices and associated methodology are described herein. Connector and connector components as well as tools associated therewith are disclosed. The connectors are preferably adapted to produce an end-to-side anastomosis at a graft/coronary artery junction. A fitting alone, or a fitting in combination with a collar may be used as a connector. Each fitting may be deployed by deflecting its shape to provide clearance for a rear segment that rotates about adjoining hinge section(s) so to fit the connector within an aperture formed in a host vessel. Upon return to a substantially relaxed position, a rear segment anchors the fitting it in place. The distal fitting may include additional side features for interfacing with the host vessel/coronary artery. The collar may include features complimentary to those of a fitting and provisions for securing the graft vessel.

45 Claims, 10 Drawing Sheets

U.S. PATENT DOCUMENTS

| | | | |
|---|---|---|---|
| 5,391,156 A | 2/1995 | Hildwein et al. | |
| 5,405,322 A | 4/1995 | Lennox et al. | |
| 5,443,497 A | 8/1995 | Venbrux | |
| 5,503,635 A | 4/1996 | Sauer et al. | |
| 5,571,167 A | 11/1996 | Maginot | |
| 5,591,226 A | 1/1997 | Trerotola et al. | |
| 5,597,378 A | 1/1997 | Jervis | |
| 5,628,784 A | 5/1997 | Strecker | |
| 5,657,429 A | 8/1997 | Wang et al. | |
| 5,665,117 A | 9/1997 | Rhodes | |
| 5,669,934 A | 9/1997 | Sawyer | |
| 5,676,670 A | 10/1997 | Kim | |
| 5,690,675 A | 11/1997 | Sawyer et al. | |
| 5,695,504 A | 12/1997 | Gifford, III et al. | |
| 5,697,968 A | 12/1997 | Rogers et al. | |
| 5,702,418 A | 12/1997 | Ravenscroft | |
| 5,713,917 A | 2/1998 | Leonhardt et al. | |
| 5,720,755 A | 2/1998 | Dakov | |
| 5,725,544 A | 3/1998 | Rygaard | |
| 5,728,133 A | 3/1998 | Kontos | |
| 5,749,375 A | 5/1998 | Maginot | |
| 5,749,895 A | 5/1998 | Sawyer et al. | |
| 5,755,775 A | 5/1998 | Trerotola et al. | |
| 5,755,778 A | 5/1998 | Kleshinski | |
| 5,762,458 A | 6/1998 | Wang et al. | |
| 5,779,718 A | 7/1998 | Green et al. | |
| 5,797,920 A | 8/1998 | Kim | |
| 5,797,934 A | 8/1998 | Rygaard | |
| 5,810,884 A | 9/1998 | Kim | |
| 5,814,005 A | 9/1998 | Barra et al. | |
| 5,824,015 A | 10/1998 | Sawyer | |
| 5,861,003 A | 1/1999 | Latson et al. | |
| 5,868,759 A | 2/1999 | Peyser et al. | |
| 5,868,761 A | 2/1999 | Nicholas et al. | |
| 5,868,770 A | 2/1999 | Rygaard | |
| 5,871,536 A | 2/1999 | Lazarus | |
| 5,931,842 A | 8/1999 | Goldsteen et al. | |
| 5,934,286 A | 8/1999 | Maginot | |
| 5,938,672 A | 8/1999 | Nash | |
| 5,938,696 A | 8/1999 | Goicoechea et al. | |
| 5,944,019 A | 8/1999 | Knudson et al. | |
| 5,944,730 A | 8/1999 | Nobles et al. | |
| 5,944,738 A | 8/1999 | Amplatz et al. | |
| 5,944,750 A | 8/1999 | Tanner et al. | |
| 5,954,735 A | 9/1999 | Rygaard | |
| 5,957,940 A | 9/1999 | Tanner et al. | |
| 5,964,782 A | 10/1999 | Lafontaine et al. | |
| 5,968,053 A | 10/1999 | Revelas | |
| 5,968,089 A | 10/1999 | Krajicek | |
| 5,968,090 A | 10/1999 | Ratcliff et al. | |
| 5,972,017 A | 10/1999 | Berg et al. | |
| 5,972,023 A | 10/1999 | Tanner et al. | |
| 5,976,178 A | 11/1999 | Goldsteen et al. | |
| 5,979,455 A | 11/1999 | Maginot | |
| 5,984,955 A | 11/1999 | Wisselink | |
| 5,989,276 A | 11/1999 | Houser et al. | |
| 5,989,287 A | 11/1999 | Yang et al. | |
| 5,993,468 A | 11/1999 | Rygaard | |
| 6,001,124 A | 12/1999 | Bachinski | |
| 6,004,347 A | 12/1999 | McNamara et al. | |
| 6,007,576 A | 12/1999 | McClellan | |
| 6,010,529 A | 1/2000 | Herweck et al. | |
| 6,017,352 A | 1/2000 | Nash et al. | |
| 6,019,788 A | 2/2000 | Butters et al. | |
| 6,030,370 A | 2/2000 | Kupka et al. | |
| 6,030,392 A | 2/2000 | Dakov | |
| 6,030,395 A | 2/2000 | Nash et al. | |
| 6,036,702 A | 3/2000 | Bachinski et al. | |
| 6,036,703 A | 3/2000 | Evans et al. | |
| 6,036,705 A | 3/2000 | Nash et al. | |
| 6,048,362 A | 4/2000 | Berg | |
| 6,056,762 A | 5/2000 | Nash et al. | |
| 6,059,824 A | 5/2000 | Taheri | |
| 6,063,114 A | 5/2000 | Nash et al. | |
| 6,068,654 A | 5/2000 | Berg et al. | |
| 6,071,305 A | 6/2000 | Brown et al. | |
| 6,074,416 A | 6/2000 | Berg et al. | |
| 6,113,612 A | 9/2000 | Swanson et al. | |
| 6,117,147 A | 9/2000 | Simpson et al. | |
| 6,120,432 A | 9/2000 | Sullivan et al. | |
| 6,149,681 A | 11/2000 | Houser et al. | |
| 6,152,937 A * | 11/2000 | Peterson et al. | 606/153 |
| 6,293,955 B1 | 9/2001 | Houser et al. | |
| 6,361,559 B1 | 3/2002 | Houser et al. | |
| 6,494,889 B1 * | 12/2002 | Fleischman et al. | 606/155 |

FOREIGN PATENT DOCUMENTS

| | | |
|---|---|---|
| EP | 0 894 475 | 2/1999 |
| WO | WO 96/22745 | 8/1996 |
| WO | WO 97/13463 | 4/1997 |
| WO | WO 97/13471 | 4/1997 |
| WO | WO 97/16122 | 5/1997 |
| WO | WO 97/27893 | 8/1997 |
| WO | WO 97/27897 | 8/1997 |
| WO | WO 97/27898 | 8/1997 |
| WO | WO 97/31575 | 9/1997 |
| WO | WO 97/40754 | 11/1997 |
| WO | WO 97/43961 | 11/1997 |
| WO | WO 98/03118 | 1/1998 |
| WO | WO 98/06356 | 2/1998 |
| WO | WO 98/07399 | 2/1998 |
| WO | WO 98/08456 | 3/1998 |
| WO | WO 98/19608 | 5/1998 |
| WO | WO 98/19618 | 5/1998 |
| WO | WO 98/19625 | 5/1998 |
| WO | WO 98/19629 | 5/1998 |
| WO | WO 98/19630 | 5/1998 |
| WO | WO 98/19631 | 5/1998 |
| WO | WO 98/19632 | 5/1998 |
| WO | WO 98/19634 | 5/1998 |
| WO | WO 98/19635 | 5/1998 |
| WO | WO 98/19636 | 5/1998 |
| WO | WO 98/19732 | 5/1998 |
| WO | WO 98/38939 | 9/1998 |
| WO | WO 98/38941 | 9/1998 |
| WO | WO 98/40036 | 9/1998 |
| WO | WO 98/42262 | 10/1998 |
| WO | WO 98/52474 | 11/1998 |
| WO | WO 98/55027 | 12/1998 |
| WO | WO 98/57590 | 12/1998 |
| WO | WO 98/57591 | 12/1998 |
| WO | WO 98/57592 | 12/1998 |
| WO | WO 99/00055 | 1/1999 |
| WO | WO 99/18887 | 4/1999 |
| WO | WO 99/38454 | 8/1999 |
| WO | WO 99/45852 | 9/1999 |
| WO | WO 99/48427 | 9/1999 |
| WO | WO 99/62408 | 12/1999 |
| WO | WO 99/62415 | 12/1999 |
| WO | WO 99/63910 | 12/1999 |
| WO | WO 99/65409 | 12/1999 |
| WO | WO 00/09040 | 2/2000 |
| WO | WO 00/15144 | 3/2000 |
| WO | WO 00/24339 | 5/2000 |
| WO | WO 00/27311 | 5/2000 |
| WO | WO 00/27313 | 5/2000 |
| WO | WO 00/40176 | 7/2000 |
| WO | WO 00/53104 | 9/2000 |
| WO | WO 01/41653 | 6/2001 |

OTHER PUBLICATIONS

U.S. Appl. No. 09/329,658, filed Jun. 10, 1999, Fleischman et al.

U.S. Appl. No. 09/654,216, filed Sep. 1, 2000, Fleischman et al.

U.S. Appl. No. 09/730,366, filed Dec. 5, 2000, Fleischman et al.

U.S. Appl. No. 09/770,560, filed Jan. 26, 2001, Whayne.

U.S. Appl. No. 09/899,346, filed Jul. 5, 2001, Whayne.

U.S. Appl. No. 09/927,978, filed Aug. 9, 2001, Fleischman et al.

Cragg, A.H. et al. (1982). "Endovascular Diathermic Vessel Occlusion," *Radiology* 144:303-308.

Gorisch, W. and Boergen, K. (1982). "Heat-Induced Contraction of Blood Vessels," *Lasers in Surgery and Medicine* 2:1-13.

Heijmen, R.H. et al. (1999). "A Novel One-Shot Anastomotic Stapler Prototype for Coronary Bypass Grafting on the Beating Heart: Feasibility in the Pig," *J. Thorac. Cardiovasc. Surg.* 117: 117-125.

Yusuf, S.W. et al., (1994)"Transfemoral endoluminal repair of abdominal aortic aneurysm with bifuricated graft" *Lancet* 344(8923):650-651.

* cited by examiner

DISTAL ANASTOMOSIS SYSTEM

CROSS-REFERENCE TO RELATED APPLICATIONS

This application claims the benefit of priority to U.S. Provisional patent application Ser. No. 60/333,276 filed Nov. 14, 2001 and is also a continuation-in-part of U.S. patent application Ser. No. 09/899,346 filed Jul. 5, 2001, now U.S. Pat. No. 6,626,920, each of which is incorporated herein by reference in their entirety.

FIELD OF THE INVENTION

This relates to producing end-to-side anastomoses, particularly in communication with coronary arteries. Accordingly, distal anastomosis connectors and associated devices are disclosed.

BACKGROUND OF THE INVENTION

Current techniques for producing anastomoses during coronary artery bypass grafting procedures involve placing a patient on cardiopulmonary bypass support, arresting the heart, and interrupting blood flow in order to suture, clip or staple a bypass graft to the coronary artery and aorta. However, cardiopulmonary bypass support is associated with substantial morbidity and mortality.

This invention provides devices and methods to avoid bypass support by allowing for positioning and securing bypass grafts at host vessel locations without having to stop or re-route blood flow. In addition, this invention mitigates risks associated with suturing, clipping or stapling the bypass graft to a host vessel. This may be accomplished, in part, by features adapted to avoid bleeding at graft attachment sites and avoiding collapse of a host vessel around the incision point. Further, the invention optionally provides features to improve blood flow within a graft and increase the patency of a graft.

In performing cardiac bypass surgery, anastomosis sites are typically provided at a proximal site along a patient's aorta, and a distal site along a coronary artery beyond a partial or complete occlusion. Producing an effective anastomosis along a coronary artery is particularly challenging. The outer diameter of a coronary artery where a distal anastomosis may be needed can range from between about 1 mm to about 4 mm in size. By way of comparison, the outer diameter of the aorta where a proximal anastomosis may be located ranges between about 20 mm and about 50 mm in size.

The relatively small size of the site for a distal anastomosis translates to greater difficulty in a number of ways. Basic surgical challenges are encountered in dealing with the smaller vasculature. Further, an interface issue is introduced. Often, particularly for connection with the smaller coronary arteries, a graft conduit will have a larger diameter than the host vessel. This may be due to the need for a larger diameter conduit to carry adequate blood flow or the result of using a saphenous vein which must be inverted for use due to its valving, thereby orienting the larger end of the graft toward the distal site. For whatever reason, the mismatch in size in joining the graft to the coronary artery must be dealt with. The present invention is adapted to handle these issues as well as others as may be apparent to those with skill in the art. The distal-type connectors described herein may be employed with precision and speed, resulting in treatment efficacy not heretofore possible.

SUMMARY OF THE INVENTION

The invention includes various improvements in end-side anastomosis systems. Particularly, connectors for producing distal anatomoses are described. They each include a fitting comprising a rear section with a segment that is deflectable about a hinge section to allow for placement and securing the device. Curvilinear side and forward-facing portions are preferred. Most preferably, these portions are configured to conform to the shape of a host vessel. Such a fitting may alone serve as a connector between a host vessel and a graft. Alternately, the connector may comprise a fitting in combination with a collar adapted to secure a graft to the fitting.

Various features for improving the deployability of a connector, hemostasis at the connector and blood flow through a graft may be provided by the invention. Further, various tools for use in preparing for and creating an end-side anastomosis may comprise part of the invention.

While connectors and deployment devices according to the present invention are preferably used in coronary artery bypass grafting procedures, particularly at a distal location, it is to be understood that the systems described herein may be used for purposes other than creating distal anastomoses. The systems may also be used to produce anastomoses between bypass grafts and host vessels to treat other occlusions, vascular abnormalities such as stenoses, thromboses, aneurysms, fistulas and indications requiring a bypass graft. The system of the present invention is also useful in bypassing stented vessels that have restenosed, and saphenous vein bypass grafts that have thrombosed or stenosed. Further, the invention may have other applications, such as producing arterial to venous shunts for hemodialysis, bypassing lesions and scar tissue located in the fallopian tubes causing infertility, attaching the ureter to the kidneys during transplants, and treating gastrointestinal defects (e.g., occlusions, ulcers, obstructions, etc.), among others.

The present invention variously includes the devices as well as the methodology disclosed. Furthermore, it is contemplated that subcombinations of features, especially of the connector features disclosed, comprise aspects of the invention.

BRIEF DESCRIPTION OF THE DRAWINGS

Each of the following figures diagrammatically illustrates aspects of the present invention. The illustrations provide examples of the invention described herein. Like elements in the various figures often are represented by identical numbering. For the sake of clarity, some such numbering may be omitted.

FIGS. 9b and 9c show side and perspective views of the collar embodiment in FIG. 9a.

DETAILED DESCRIPTION OF THE INVENTION

The variations of the invention discussed herein are applicable to robotic surgery and less invasive (i.e., minimally invasive) surgery involving a thoracostomy or mini median sternotomy to access the anastomosis site as well as the surgical approaches, such as that described below. As noted above, the present invention includes variations of anastomosis connectors having features adapted to perform distal anastomoses. Anastomosis connectors, tools and associated methodology for producing proximal and distal anastomoses are described variously in U.S. and foreign patent and applications entitled, "Percutaneous Bypass Graft and Securing System", U.S. Pat. No. 5,989,276; "Percutaneous Bypass Graft and Securing System", U.S. patent application Ser. No. 09/415,776; Percutaneous Bypass Graft Securing System", PCT Publication No. WO 98/19625; "Sutureless Anastomosis Systems", U.S. patent application Ser. No. 09/329,503; "Sutureless Anastomosis Systems", PCT Publication No. WO 99/65409; "Thermal Securing Anastomosis Systems" U.S. patent application Ser. No. 09/329,504; "Thermal Securing Anastomosis Systems", PCT Publication No. WO 99/63910; "Aortic Aneurysm Treatment Systems", U.S. patent application Ser. No. 09/329,658; "Aortic Aneurysm Treatment Systems", PCT Publication No. WO 00/15144; "Additional Sutureless Anastomosis Embodiments", U.S. patent application Ser. No. 09/654,216; "Improved Anastomosis Systems", U.S. patent application Ser. No. 09/730,366; "End-Side Anastomosis Systems", PCT Publicatioin No. WO 01/416653; "Advanced Anastomosis Systems (II)", U.S. patent application Ser. No. 09/770,560; "Distal Anastomosis System", U.S. patent application Ser. No. 09/899,346; "Distal Anastomosis System", U.S. Patent Application Ser. No. 60/333,276; and "Sutureless Anastomosis System Deployment Concepts", U.S. patent application Ser. No. 09/927,978 and applications and patents claiming benefit hereto, all commonly owned by Converge Medical, Inc. and all incorporated herein by reference in their entirety.

Figure 1:
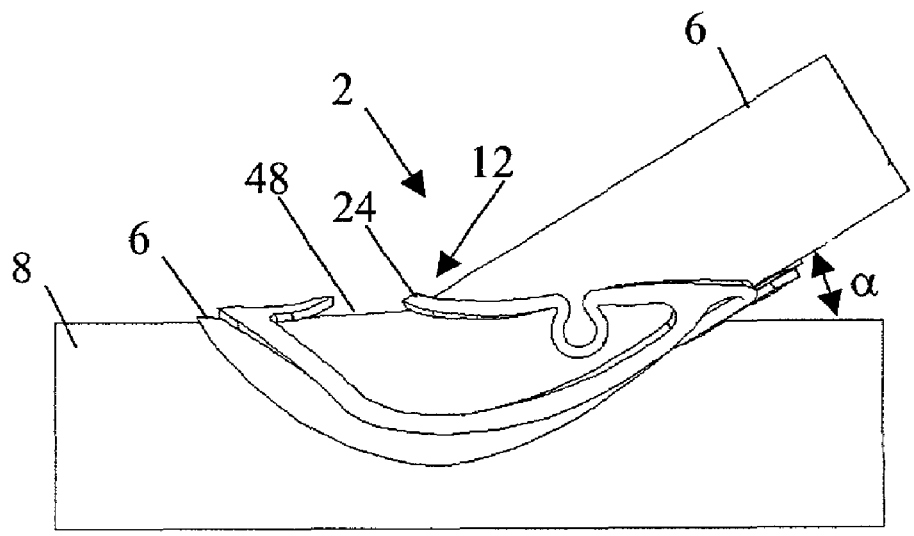
FIG. 1 shows a side view of an installed connector with a collar that secures a graft to the connector and affixes the connector and graft assembly to a vessel wall.
Figure 2:
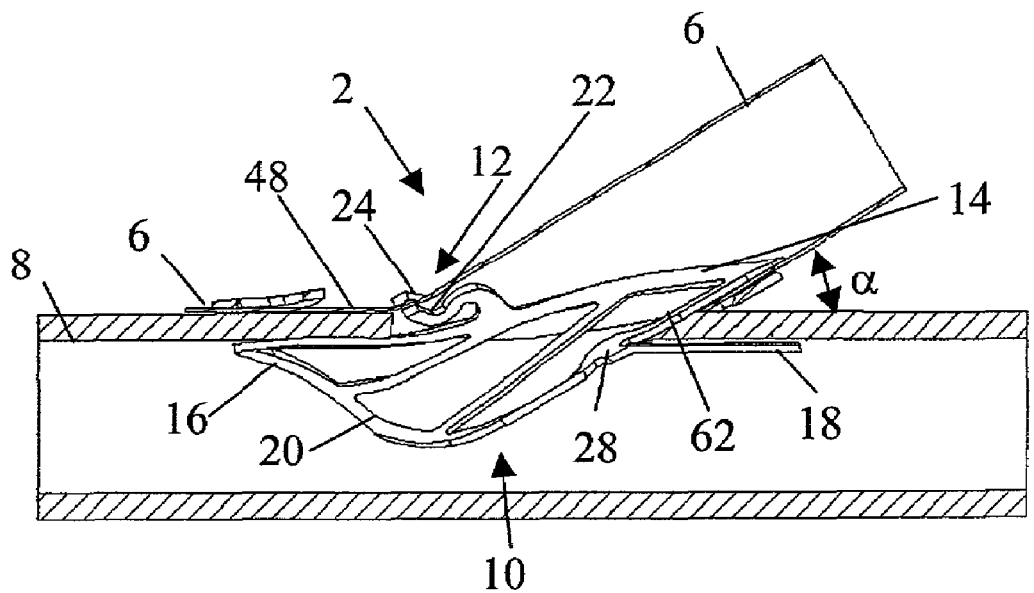
FIG. 2 shows a side-sectional view of the installed connector and collar in FIG. 1.

FIGS. 1 and 2 show distal anastomoses (2) formed by connectors (4) according to the present invention. Each connector (4) attaches a graft (6) to a host vessel (8). In this case, the host vessel is a coronary artery. Graft (6) preferably comprises a saphenous vein, radial artery, left internal mammary artery, or right internal mammary artery, though a synthetic graft (such as one made of expanded PTFE) can be utilized. The connector in FIG. 1 includes a fitting (hidden) secured to the graft and the host vessel with a collar (12). FIG. 2 shows a side-sectional view of the connector in FIG. 1.

Referring to FIG. 2, various features of fitting (10) may be observed. First, it is noted that fitting and attached graft (6) are preferably configured so its base or body (14) is at an angle a with respect to host vessel (8). Connectors (2) are shown at approximately a 30° angle. Preferred angles for distal anastomosis range from about 20° to about 70°. A more preferable range is from about 30° to about 60°. Most preferably, they are between about 30° and about 45°. The angle may help maintain hemostasis and optimal blood flow once the anastomosis is created and retracted organs and tissue bear upon the site. Pressure created by such action will not dislodge connector (4) or kink or collapse graft (6) since the angle preferably allows graft (6) to leave the connector (4) and lie substantially in line with the heart. In addition to improving blood-carry capability of the conduit in assuring stability of the connector, including some angle in the connector enables the manner of deployment taught below.

Fitting (10) may include at least a front or leading segment (16) and a rear or trailing segment (18). When situated to form an anastomosis, these segments preferably lie approximately in line with host vessel (8). So-placed, they prevent removal of the connector from the host vessel. Optional lateral or side portions (20) may also aid in this regard. This is especially the case in forming an anastomosis with a very small diameter vessel (such as a 1 to 4 mm diameter coronary artery). Furthermore, lateral portions (20) may assist in providing a physical barrier to leakage. This may be true irrespective of the size of host vessel (8). The use of one or more lateral portions (20) on each side of fitting (10) may also provide a smooth transition between the leading and trailing portions of fitting (10) to help moderate or alleviate trauma to the interior of the host vessel (8).

A lateral portion may be provided integrally with a form providing at least part of leading segment (16) and trailing segment (18). This continuous coverage helps to ensures complete tissue capture between the fitting (10) inside the host vessel and the collar (not shown) outside the host vessel. Complete coverage ensures hemostasis at the vessel to graft interface.

Figure 3A:
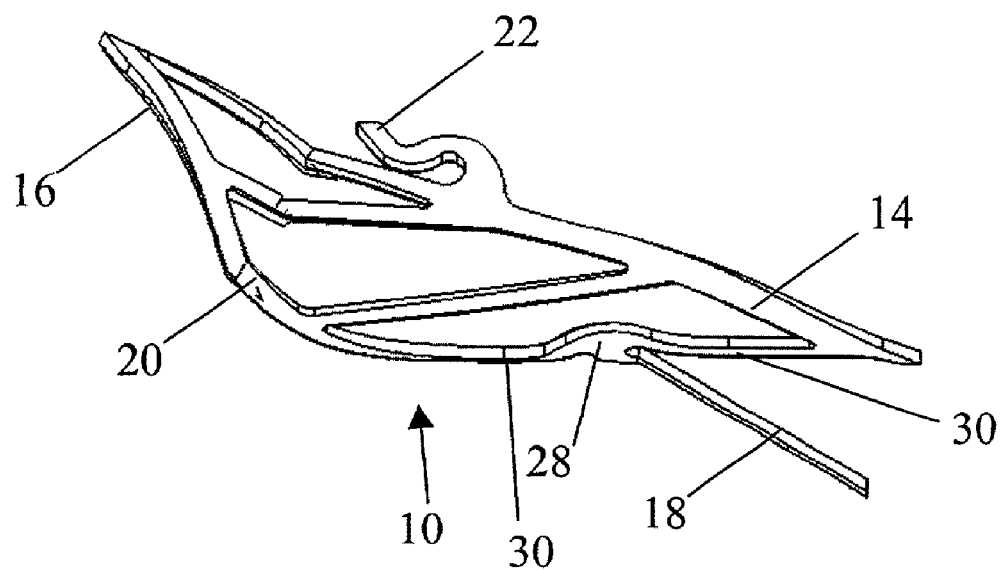
FIGS. 3a and 3b show side and isometric views of a formed connector as may be used according to that shown in FIGS. 1 and 2.
Figure 7A:
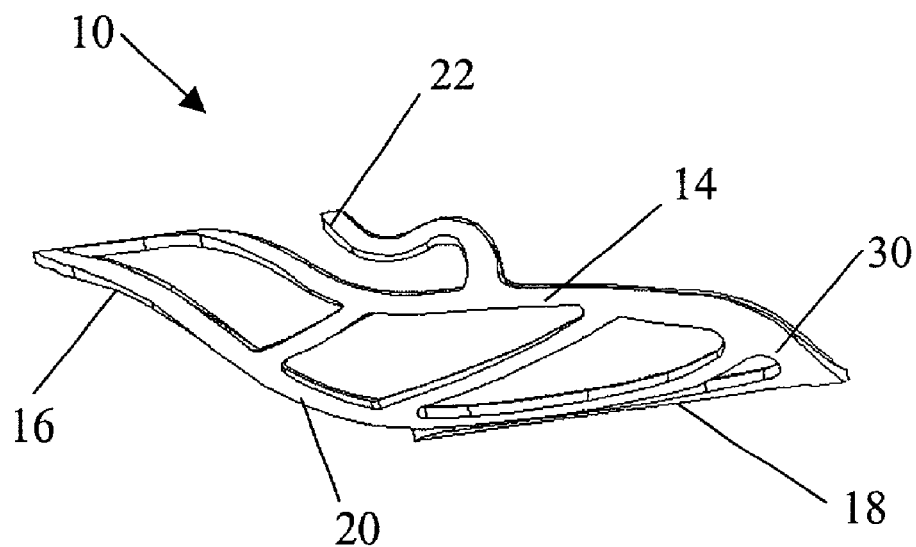
FIGS. 7a and 7b show side and perspective views of the non-formed connector in FIG. 6.

Additional optional features of fitting (10) include tabs (22) to assist in securing graft (6) and/or optional collar (12). Such tabs may be oriented to grip graft (6) as shown in FIG. 2. One or more tabs may also be adapted to form a locking interface with one or more complementary tabs (24) optionally included in collar (12). Also, the height or amount of material incorporated in the base of the fitting may be varied. In order to utilize as little material as possible to join the various segments, base (14) may be provided by a narrow band of material as shown in FIGS. 3a, 7a or otherwise. To achieve proper relative placement of these features, base (14) may be curved or undulate.

Figure 3B:
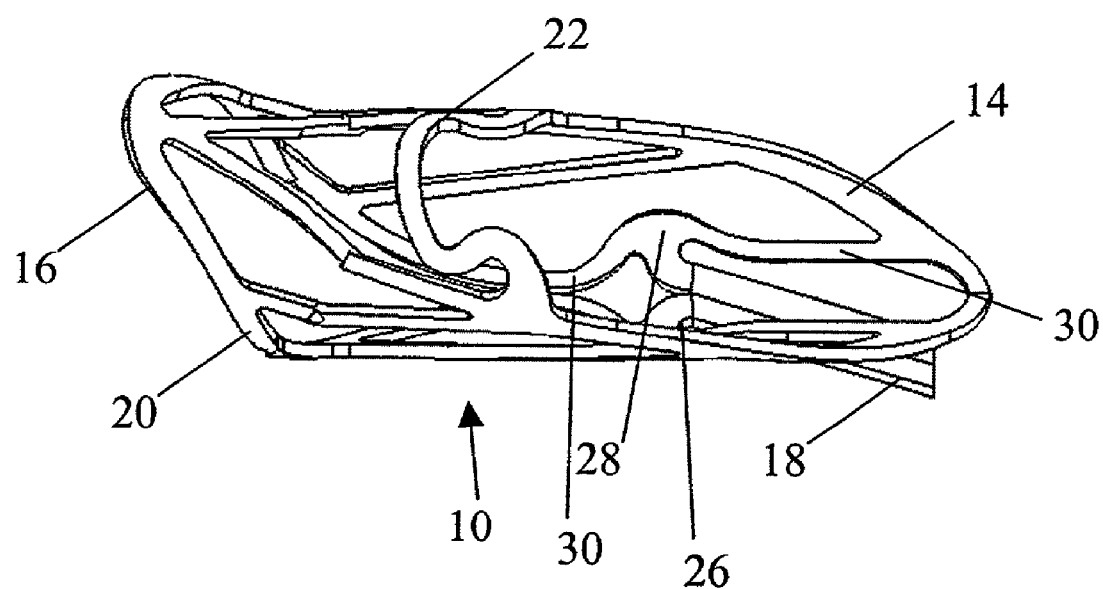

As shown in FIG. 3B, the connector opening (26) may have an ovalized opening to the anastomosis or have a circular bore. As will be discussed below, the connector is preferably fabricated from a raw tube that is laser cut into the desired pattern and thermally formed into the desired resting configuration as shown in FIGS. 3a and 3b. This inherent circular profile may be altered by closing the width between opposite sides of the base (14) causing the connector to assume an ovalized profile with the major axis extending from the leading segment (16) towards the trailing segment (18) and the minor axis perpendicular to the major axis. Configuring fitting (10) with an ovalized opening (26) may be useful in providing an interface at a smaller host vessel. It provides a manner in which to account for the size difference between the vessel and what is often a larger opening of the graft by transitioning the geometry change from the circular graft cross-section to an ovalized anastomosis cross-section. The ovalization increases the available perimeter to accommodate a host vessel without increasing the lateral size of the connector. Instead, a connector may be lengthened. This will usually be an acceptable alteration in connector geometry since only the size of the arteriotomy made in the host vessel need be lengthened to fit the connector in place.

Figure 6:
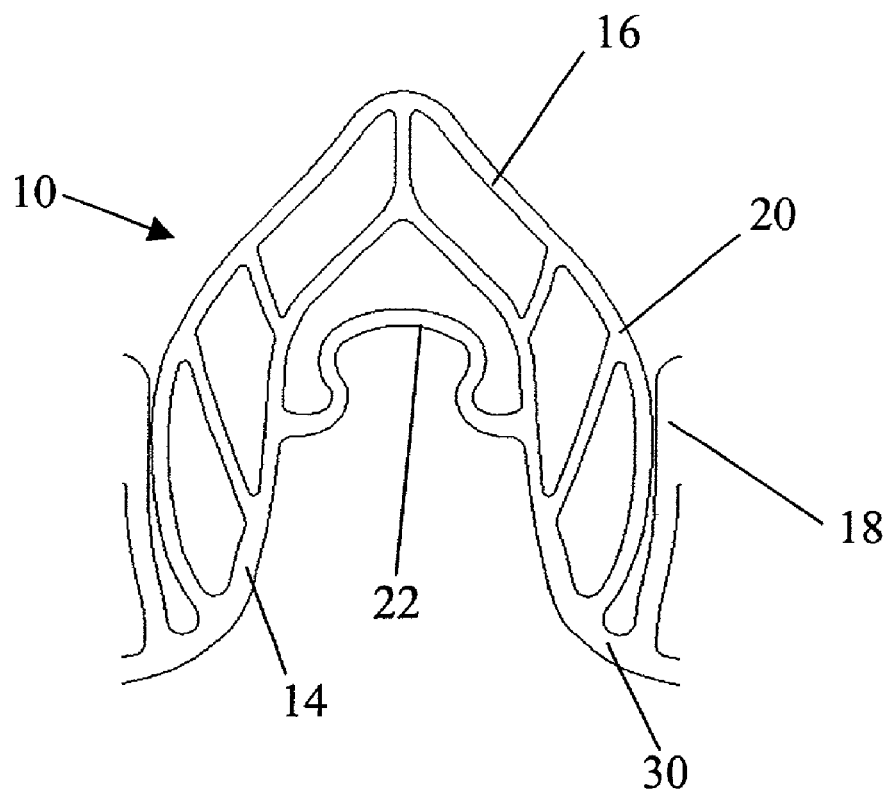
FIG. 6 shows a flattened view of an alternative connector embodiment.

Features that are preferably required of fitting (10), in addition to the basic leading and trailing segment configuration, are found in connection with a hinge section (28), shown in FIGS. 2, 3a and 3b. Hinge section (28) may be provided in a number of configurations. However, the configurations serve the same purpose. Each of the variations shown and described allow rear segment (18) to be displaced sufficiently to clear the host vessel wall for insertion of the connector into the host vessel by significant torsional deflection of areas between rear segment (18) and fitting body (14). In the fitting variations shown in FIGS. 2, 3a and 3b, a pair of torsion sections (30) are presented on each side of rear segment (18). In the variation in FIGS. 6, 7a and 7b, hinge section (28) may include only one torsion section (30) on each side of rear segment (18).

To displace rear segment (18) sufficiently, the rotation about torsional sections may account for a substantial amount of the displacement required of trailing segment (18). The additional displacement may arise from bending of the trailing segment (18) relative to the junction between the trailing segment and the torsional sections. In the variation of the fitting shown in FIGS. 6, 7a and 7b, rotation of rear segment (18) occurs about the pair of torsional members (30), whereas in the variations in FIGS. 2, 3a and 3b, the rotation that occurs is shared between two pair of torsional sections.

Such dual action provides for certain advantages notable in the variations shown in FIGS. 2, 3a and 3b. Namely, upon forward deflection of rear segment (18), the lateral portions connected to torsional sections are caused to be drawn or flexed inward. This action facilitates introduction of connector (4) into host vessel (8) by clearing portions that could otherwise interfere with entry. In addition, the inherent design of the embodiment in FIGS. 2, 3a and 3b may require a pair of torsional sections on each side of the trailing section, one integrated with the base (14) and an opposite extending one integrated with the leading section (16). The embodiment in FIGS. 2, 3a and 3b has the trailing section (18) cut from the base (14) and deflected approximately 30 degrees in its resting configuration. This is highlighted by the difference in shape between the laser cut manufacturing step shown in FIGS. 4a and 4b and the thermally formed configuration shown in FIGS. 3a and 3b. As such, the trailing section (18) may be integrated with the base and the leading section to provide a continuous band of support throughout the anastomosis along the interior surface of the host vessel, increase the resistance to deflection, once the connector is deployed, and providing a wedge between the trailing section (18) and the base (14) capable of increasing the compression forces that the trailing section (18) and the base (14) exert against the graft and the host vessel to ensure hemostasis at the heel of the anastomosis.

Figure 7B:
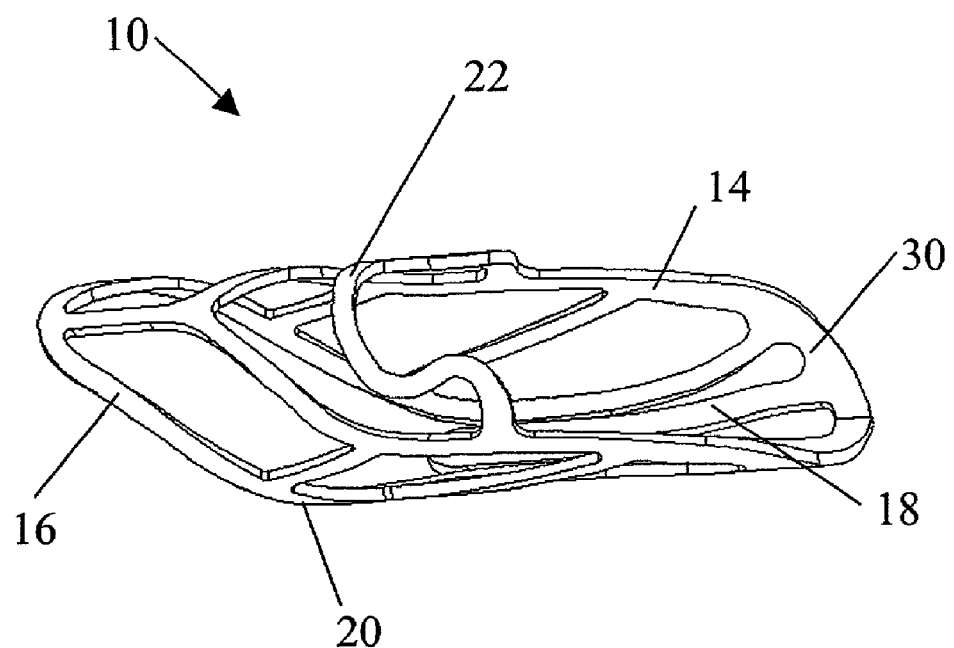
Figure 8:
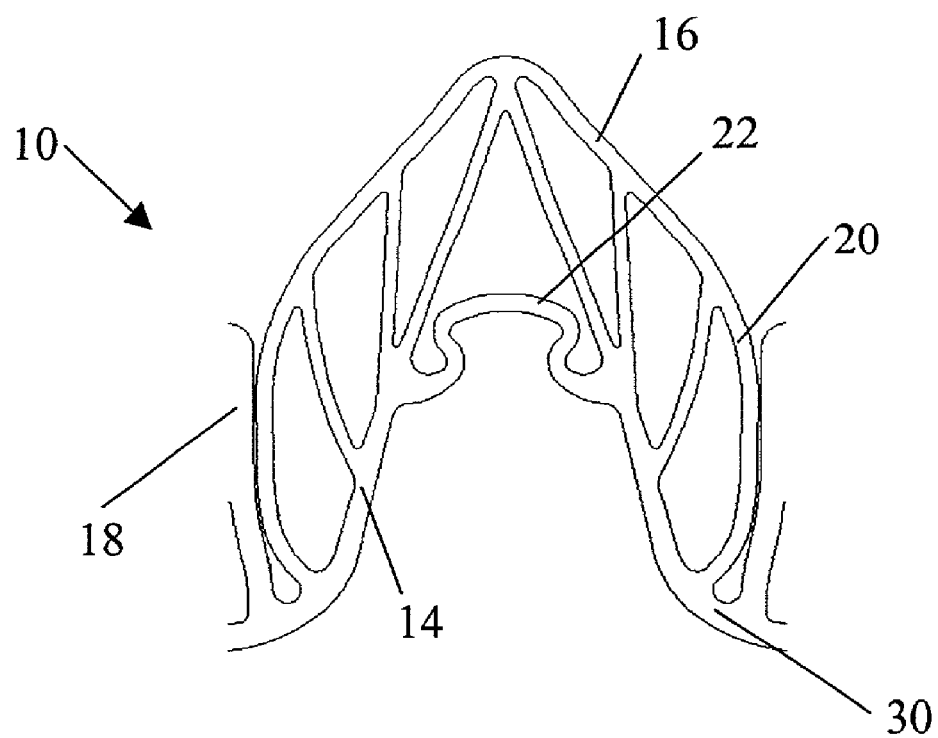
FIG. 8 shows a flattened view of another connector embodiment.

For fittings configured similarly to that in FIGS. 7a and 7b, it is also noted that rotation of members (30) in deflecting rear section forward may cause lateral portions (20) to be drawn inward to some extent. However, the amount of inward deflection may be less relative to the variations of the fitting shown in FIGS. 2 and 3a and 3b where lateral portions (20) are directly connected to torsional sections.

Figure 9A:
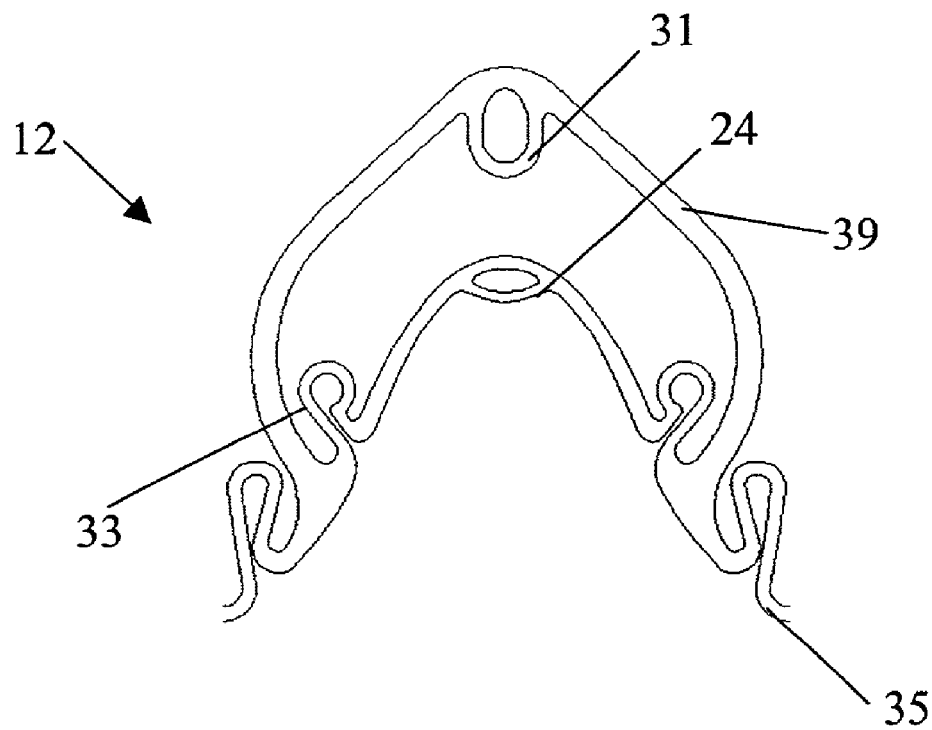
FIG. 9a shows a flattened view of a collar embodiment.
Figure 9B:
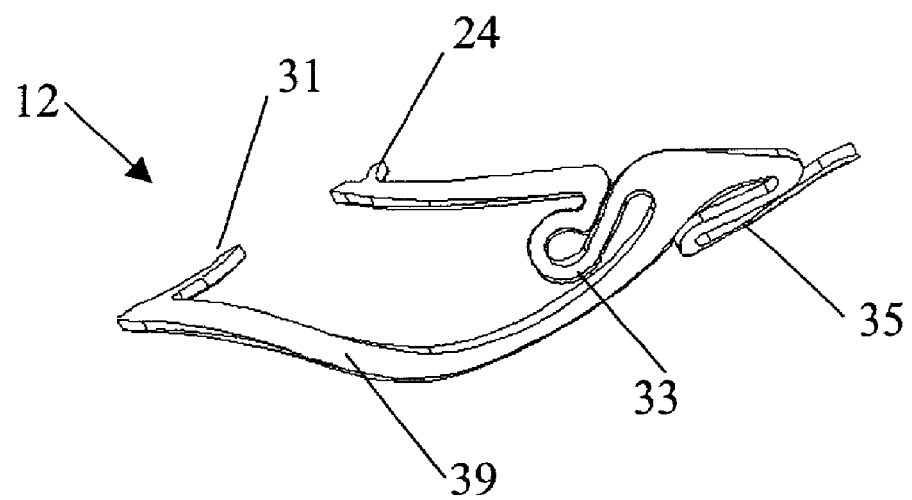
Figure 11:
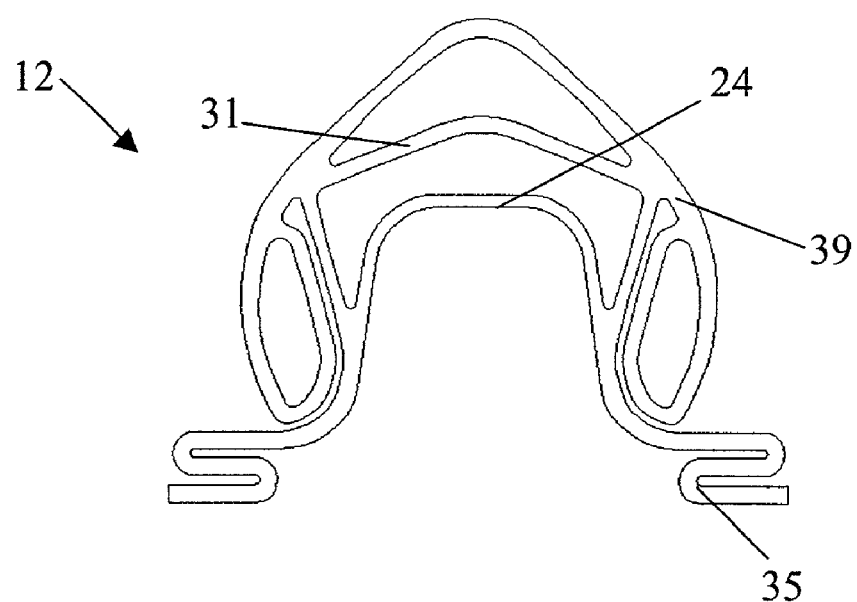
FIG. 11 shows a flattened view of an alternative collar embodiment.

Turning now to the features of collar (12), FIGS. 1, 9a and 9b illustrate desirable features of this part of connector (4). One purpose of collar (12) is to secure graft (6) to fitting (4) and ensure the graft produces a gasket against the host vessel throughout the periphery of the anastomosis to ensure hemostasis. As noted above, optional collar tab(s) (24) may assist in this regard by interfacing with optional fitting tab(s) (22). Also, collar (12) may be made to be resiliently biased against graft (6) to hold it to fitting (4). Further, expansion spring members (35) may be provided to enable expanding the diameter of the collar for placement around the fitting and returning the collar towards its preformed configuration once positioned to ensure a secure fit of collar (12) about fitting (6). The expansion spring members (35) in the embodiment in FIGS. 1, 9a and 9b may incorporate a vertical undulating pattern which straightens as the collar is expanded from its resting diameter towards an enlarged geometry and urges. Once the external force enlarging the collar is removed, the expanding spring members may recoil towards the undulating pattern urging the collar towards its resting, smaller diameter configuration. FIG. 11 shows an alternative expansion spring member (35) which involves a horizontal undulating pattern. In this embodiment, enlargement of the expansion spring member (35) causes the central piece to deflect towards the base (14) of the fitting ensuring the collar maintains contact with the fitting despite enlargement or other deflection of the collar. This may become effective when the collar is deflected during deployment which may cause slight expansion of the collar to ensure separation between the collar components and the fitting during insertion into the host vessel, as will be discussed below. Provision of expansion spring members (35) eliminates any perceived need to use a locking member such as hook interlocking mechanism, a retaining clip, suture, implantable clips, staples, or other device that might be desired to ensure graft (6) is secured to fitting (4).

Figure 9C:
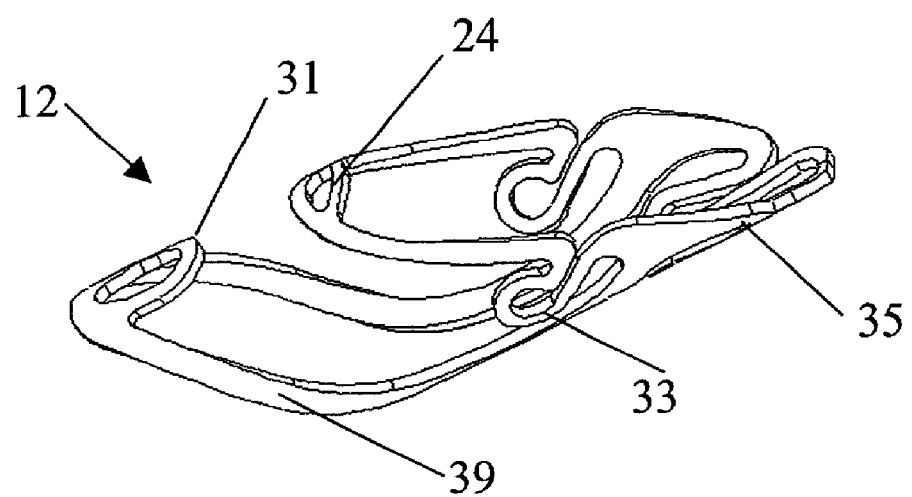

Preferably, the distal band (39) of the collar (12) extends completely around the anastomosis from the heel to the toe to overlap or interface with corresponding lateral features (20) of a complimentary fitting (10) to form a complete seal at an anastomosis site. Likewise, the shape of the bore of the collar as shown in FIG. 9c preferably complements that of the fitting. In instances where the fitting has a circular bore (26), at least a mating portion of collar (12) is preferably substantially circular as well. In instances where fitting bore (26) is ovalized, a corresponding shape is preferably utilized in collar (12). The distal band (39) is secured to the base of the collar at the heel to enable deflecting the distal band (39) upward during deployment. The semicircular nature of the distal band (39) may cause the distal band to buckle outward as it is deflected with a deployment tool. This provides separation between the distal band (39) and the lateral sections (20) of the fitting to ensure host vessel tissue can enter this gap such that once positioned, the distal band may be released thereby compressing the graft and the host vessel against the fitting leading section and lateral section ensuring complete hemostasis around the periphery of the anastomosis.

Figure 10A:
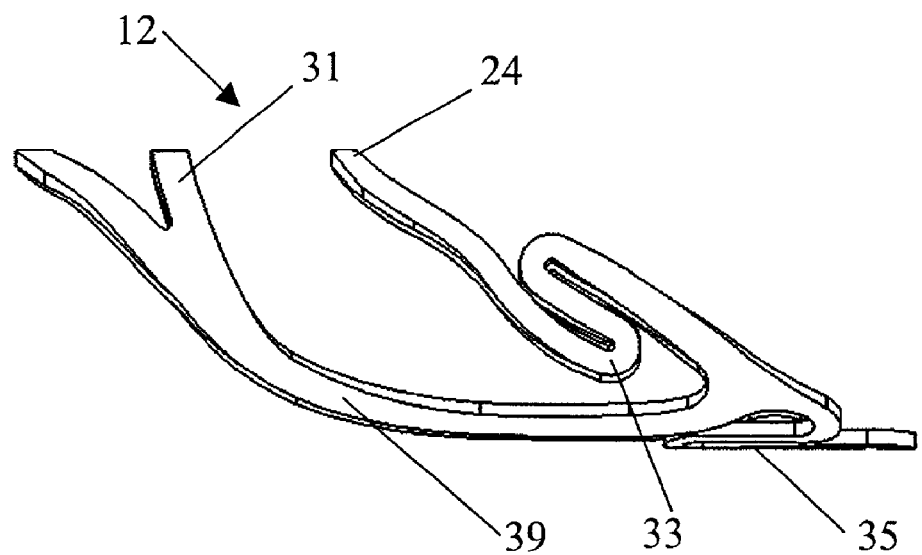
FIGS. 10a and 10b show side and perspective views of another collar embodiment.
Figure 10B:
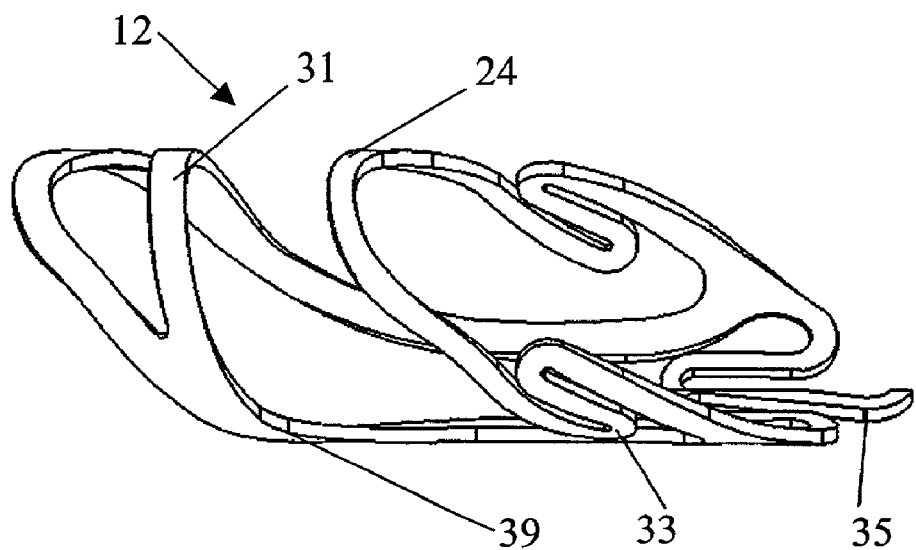

Other features of the collar (12) embodiment shown in FIGS. 1, 9a–9c involves side spring loops (33). These side spring loops (33) may serve dual purposes: they may enable axial extension of the tab (24) during loading of the collar over the graft and the fitting to enable placing the tab (24) of the collar into engagement with the tab (22) of the fitting without requiring significant manipulation of the fitting and collar. The side spring loops (33) may also provide an engagement point for pins of a deployment tool to stabilize the connector during deployment or a loading tool to manipulate the collar during placement of the graft and/or locking of the fitting to the collar. In the former, the side spring loops (33) may or may not be thermally formed in a radially outward configuration such that the deployment tool pins may be readily inserted from the top, front, or rear, depending on the location of the pins on the deployment tool. As shown in FIGS. 10a and 10b, the side spring loops (33) may alternatively be fabricated without a loop but with horizontal (or vertical) undulating members that straighten as the tab (24) is extended relative to the base of the collar.

The collar embodiments in FIGS. 9a–9c and 10a–10b may also incorporate a grasping loop or link (31) that provides an exposed edge which the deployment tool may engage and deflect the distal band (39) relative to the base of the collar. The facilitates engagement and removal of the deployment tool relative to the collar.

Whether prepared in connection with a collar or not, connector (4) is preferably installed at an anastomosis site as shown in FIG. 2. Here, it may be observed that graft toe (48) preferably overlaps host vessel (8). A heel portion (62) may abut, overlap host vessel (8) or leave a slight gap. When a connector is provided with a collar (12), the visible result will resemble that in FIG. 1. Still, the preferred relation of graft (6) to host vessel (8) remains similar to that shown in FIG. 2, depending on the fitting configuration selected.

Now that many of the device features of the invention have been described, the methodology associated therewith is set forth in the order in which it is preferred that a surgeon or surgical team take action to perform a coronary bypass procedure. Variation of this procedure is, of course, contemplated. Furthermore, it is to be understood that the devices described herein may be used outside of this context.

This being said, after opening a patient and taking a measurement between intended target sites for proximal and distal anastomoses, a graft member (6) of sufficient length may be obtained. Typically this will be a saphenous vein. Alternately, another harvested vessel (such as the left internal mammary artery, right internal mammary artery, or radial artery), a synthetic vessel or a donor vessel may be used as a graft.

Especially in the case where an organic member is used, the vessel is preferably sized to determine the appropriate connector size. This is preferably done with reference to the inner diameter (90) of the graft by inserting pins of increasing size (e.g. by 0.25 increments) until the graft no longer easily fits over a given pin. The size of the largest pin over which graft easily fits over sets the inner diameter of the graft.

Next, a connector for producing an anastomosis at a desired angle, and having an appropriate size may be chosen. The size of fitting (10) and optional collar (12) is preferably the first incremental size over the inner diameter of the graft. It is contemplated that connector component sizes may be sized to fit grafts of a diameter from about 2 mm to about 6 mm progressively, at 0.5 mm increments.

Once appropriately sized connector components are chosen, a graft may be skeletonized about 10 mm away from the end to be used in connection with the distal anastomosis. This may be accomplished by holding the adventitial tissue away from the graft with forceps and removing selected portions with Potts scissors. At this stage, graft (6) may be cut in such a manner as discussed above and advanced over fitting (10) into a position as depicted in FIG. 1, or 2.

Advancing graft (6) through collar (12) may be accomplished while holding the collar in an enlarged configuration with a loading tool or clamp (e.g., a hemostat) and using forceps to pull graft through collar. Then, the fitting (10) may be inserted through the cut end of the graft until the trailing segment of the fitting abuts the expansion spring of the collar. This ensures that the graft is completely captured between the fitting and the collar, which may be essential to ensuring hemostasis at the anastomosis. Once in place over a fitting (18), graft (6) may be trimmed to more closely conform to the shape of connector elements, particularly the exterior of any collar (12) used. Trimming a graft in this manner may be particularly appropriate in instances where the graft used is simply prepared by taking a vessel, cutting it at 90° relative to its length and then creating a rear slit along its length as described above.

In placing fitting (10) into graft (6), it is to be set in relation to collar (12) in a complementary manner. When optional tabs (22) and (24) are provided, these features can easily be used to help align a fitting and a collar relative to each other. Either way, once collar (12) and fitting (10) are properly aligned, collar (12) may be released onto graft (6). Following this, any tabs and/or locking features (36) may be engaged with each other and a final check is made to ensure accurate component placement and graft coverage.

In the event a proximal connector is to be used to complete a coronary bypass procedure, it may be connected to graft (6) in a similar fashion or as described variously in the references cited above. Still, as noted above, a distal connector may alone be used, with the proximal anastomosis to be accomplished otherwise. While it need not be the case, the distal connector will preferably be deployed before making the proximal connection.

Once a graft/connector combination is prepared, the assembly is then preferably engaged with a deployment device (not shown).

Figure 12A:
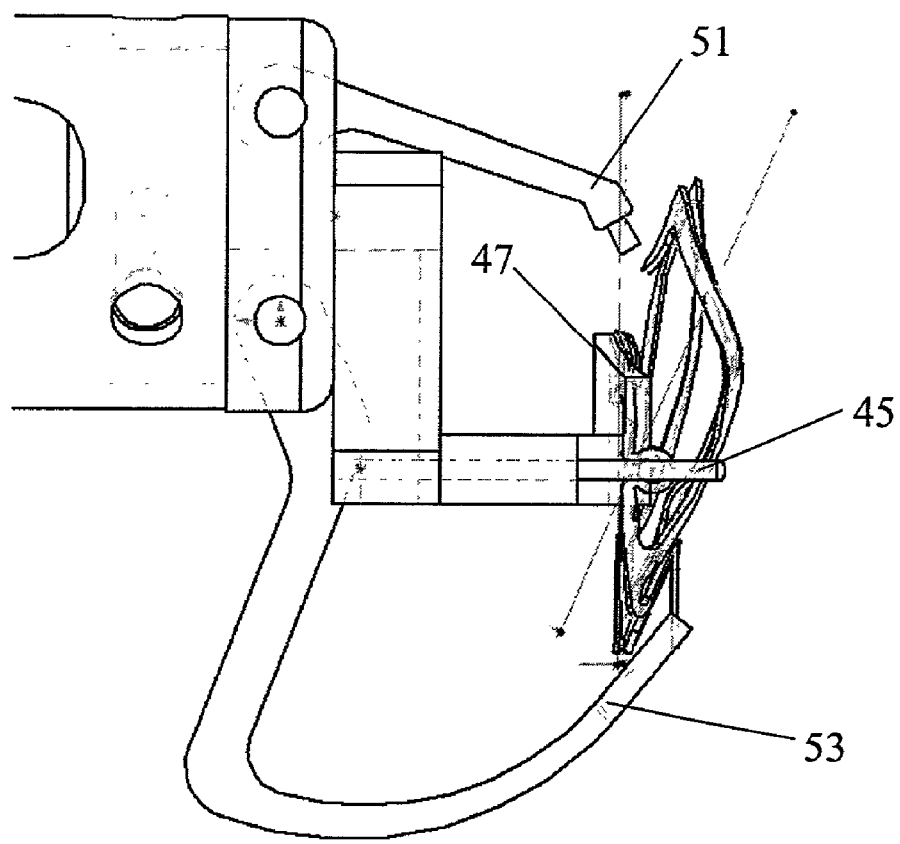
FIGS. 12a and 12b show side views of a delivery tool used to deflect the connector and collar assembly during deployment.
Figure 12B:
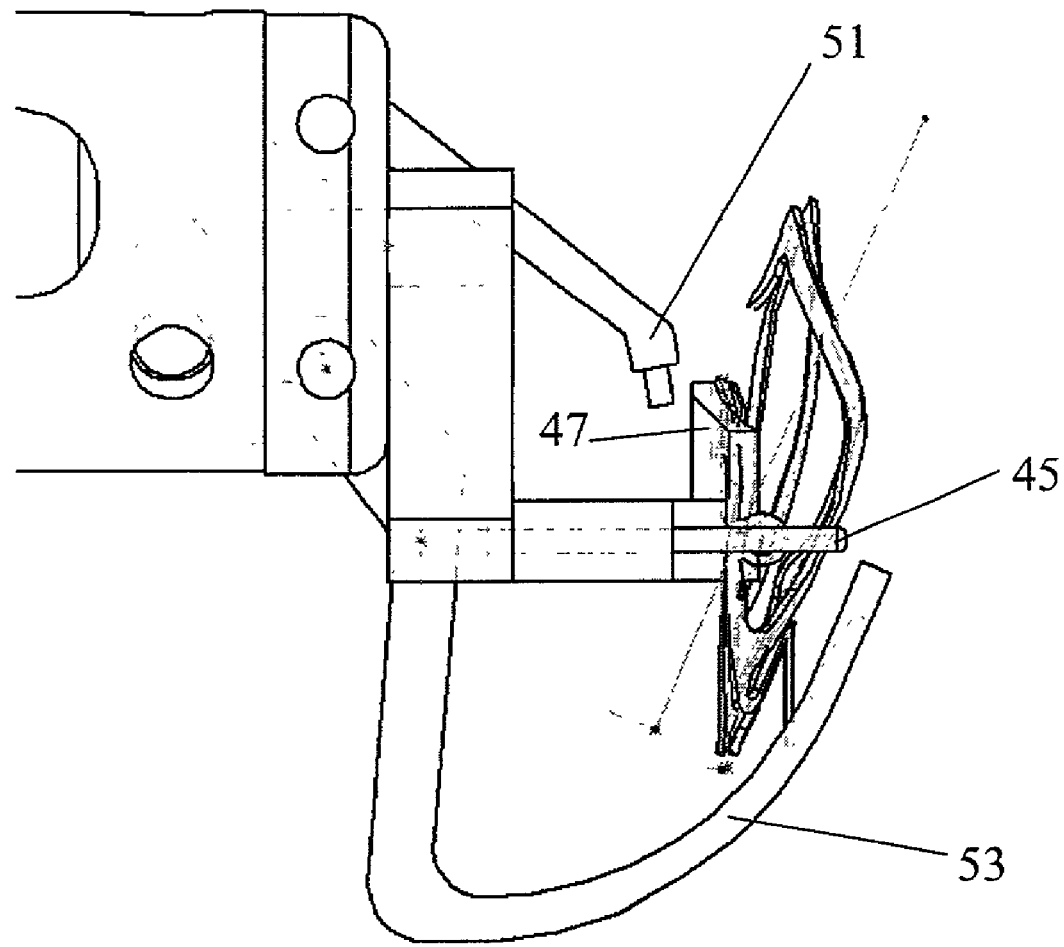

It is preferred that connector (4) be set and prepared for deployment within a deployment device, as shown in FIGS. 12a and 12b, before taking invasive action at the target site for a distal anastomosis. Regardless, a distal anastomosis site is prepared by creating an initial puncture, for instance, with the tip of a number 11 blade scalpel. Next, this opening is preferably extended longitudinally with scissors to about 3 mm to 7 mm in length depending on the vessel size. Most often, a longitudinal slit of about 5 mm is preferred. Scissors are advantageously provided in connection with an instrument. Otherwise, standard Potts scissors may be used.

The deployment tool in FIG. 12a incorporated pins (45) that may engage the spring loops of the collar. This provides stabilization of the connector relative to the deployment tool and provides a reference from which to deflect the distal band (39) of the collar. It should be noted that the deployment tool may alternatively incorporate a clamping or other grasping mechanism to engage the base of the collar and/or fitting without having to penetrate components of either the collar or fitting. One such component is a stabilization platform (47) incorporated in the deployment tool and configured to engage the front and/or lateral surface of the connector to maintain the position of the connector during deployment.

The deployment tool may also incorporates a toe deflector (51) and a heel deflector (53) which deflect and release the distal band (39) of the collar and the trailing section (18) of the fitting during deployment. FIG. 12a shows the toe deflector (51) and the heel deflector (53) in the loading or release state. FIG. 12b shows the toe deflector (51) and the heel deflector (53) in the actuated state, ready for deployment of the connector. It should be noted that in FIG. 12b, the components of the connector are not shown deflected; in operation, movement of the toe deflector and heel deflector may cause their counterparts on the connector to correspondingly deflect for deployment. Once deployed, the heel deflector and toe deflector are released enabling the trailing section of the fitting and the distal band of the collar to return towards their resting configuration causing the tissue (host vessel and graft) residing between the fitting and the collar to be compressed, like a gasket, and ensure hemostasis at the anastomosis. It should be noted that the toe deflector and the heel deflector may be actuated simultaneously; the toe deflector may be offset from heel deflection to enable full deployment of the trailing section of the fitting prior to full release of the distal band of the collar; or may be operated independently.

With the trailing segment and the distal band deflected into the deployment configuration, connector (4) is deployed. This is preferably performed by advancing leading section (16) through the arteriotomoy, and then such lateral features (20) of fitting (10) as may be provided. Deflected rear segment (18) may then be advanced into host vessel (8) and released to assume a position as shown in FIG. 2 in order to secure the connector. Particularly in those variations of the invention as described above where movement of rear segment articulates side portions (20), movement of rear segment (18) to an host-vessel engaging position will also cause affected side portions (20) to engage the sides of host vessel (8) to maintain connector (4) in place.

In instances when a collar (12) is used in connector (4), it may also be released to compress front portion (48) of graft (6) against host vessel (8). Release of collar (12) may also result in compressing graft (6) against portions of host vessel (8) opposed by lateral fitting portions (20), especially when the lateral portions are integrated with the trailing segment.

Once in place, the completed anastomosis may be checked for leakage. This may be done before and/or after an anastomosis at the proximal site is complete. At minimum, an inspection of the distal connection is preferably made when blood is flowing through graft (6). If leakage is detected and it cannot be remedied by adjustment of the graft or collar, the anastomosis site may be packed or bioglue (e.g., as available through Cryolife in Kennesaw, Ga.) or a stitch of suture material may be applied.

In extremely rare instances where these steps do not prove adequate, it may be necessary to remove connector (4). After removing with any supplemental means applied in effort to provide hemostasis, connector (4) may be removed by reversing the procedure for its deployment.

Now, returning to the elements of connector (4), optional inventive features and a manner of manufacture is described. A preferred manner of producing connector components according to the present invention is by machining tubing to include features that may be bent and set into shape to produce connector elements like those depicted in FIGS. 1, 2, 3A, 3B, 4A, 4B and 12A. Shapes so produced may be referred to as wireforms.

The machining may be accomplished by electron discharge machining (EDM), mechanically cutting, laser cutting or drilling, water-jet cutting or chemically etching. It is to be noted that portions of the connectors may be fabricated as separate components and bonded by spot welding, laser welding or other suitable manufacturing process to form complete structures. Typically, after whatever cutting or forming procedure is employed, the material may be set in a desired final shape. Where a metal is used, one or more flexure steps followed by heating will accomplish this. If the connector elements are made of alternate material such as a plastic or a composite, other forming procedures as would be apparent to one with skill in the art may be used.

Preferably, connector elements are made from a metal (e.g., titanium) or metal alloy (e.g., stainless steel or nickel titanium). Other materials such as thermoplastic (e.g., PTFE), thermoset plastic (e.g., polyethylene terephthalate, or polyester), silicone or combination of the aforementioned materials into a composite structure may alternatively be used. Also, connectors fabricated from nickel titanium may be clad with expanded PTFE, polyester, PET, or other material that may have a woven or porous surface. The fittings may be coated with materials such as paralyne or other hydrophilic substrates that are biologically inert and reduce the surface friction.

To further reduce the surface tension, metallic or metallic alloy fittings may be electropolished. Evidence suggests that electropolishing reduces platelet adhesion because of the smooth surface. Alternatively, the fittings may be coated with heparin, thromboresistance substances (e.g., glycoprotein IIb/IIIa inhibitors), antiproliferative substances (e.g., rapamycin), or other coatings designed to prevent thrombosis, hyperplasia, or platelet congregation around the attachment point between the bypass graft and the host vessel. Alternatively, a material such as platinum, gold, tantalum, tin, tin-indium, zirconium, zirconium alloy, zirconium oxide, zirconium nitrate, phosphatidyl-choline, or other material, may be deposited onto the fitting surface using electroplating, sputtering vacuum evaporation, ion assisted beam deposition, vapor deposition, silver doping, boronation techniques, a salt bath, or other coating process.

A still further improvement of the fittings is to include beta or gamma radiation sources on the end-side fittings. A beta or gamma source isotope having an average half-life of approximately 15 days such as Phosphorous 32 or Paladium 103 may be placed on the base and/or petals of the end-side fitting using an ionimplantation process, chemical adhesion process, or other suitable method. Further details as to optional treatments of connectors according to the present invention are described in 10.00. Of course, connector fitting (10) and any associated collar (12) may be made differently. To avoid electrolytic corrosion, however, dissimilar metals should not be used.

Preferably, NiTi (Nitinol) tubing or flat stock may be used to produce connector components. Irrespective of material format, a preferred alloy includes a 54.5–57% Ni content, and a remainder Ti by weight (less minor amounts of C, O, Al, Co, Cu, Fe, Mn, No, Nb, Si and W) is used. Such alloy has an $A_f$ for at about −10 to −15° C. Consequently, for typical handling and in use, the material will exhibit superelastic properties as is most desired.

Still, it is contemplated that connectors according to the present invention may utilize thermoelastic or shape memory characteristics instead, wherein the material of either or both fitting (10) and connector (12) change from a martinsitic state to an austenitic state upon introduction to an anastomosis site and exposure to a sufficiently warm environment. Taking advantage of the martinsitic state of such an alloy will ease deflecting rear segment (18) and distal band (39) and maintaining their positions until placement.

Utilizing either thermoelastic or superelastic properties makes for a connector that can have certain members stressed to a high degree and return without permanent deformation from a desired position. However, it is contemplated that either or both fitting (10) and collar (12) may be made of more typical materials such as stainless steel or plastic. For fitting (10), this is feasible in view of the manner in which rear segment (18) is displaced for insertion into a host vessel. Hinge section (28) may permit designs in which the stress applied by torsion is lower that applied in simply deflecting a rear petal or segment as shown and described in U.S. and foreign patents and applications entitled, "Improved Anastomosis Systems", U.S. patent application Ser. No. 09/730,366; "End-Side Anastomosis Systems", PCT Publication No. WO 01/41653; "Advanced Anastomosis Systems (II)" U.S. patent application Ser. No. 09/770,560.

Figure 4A:
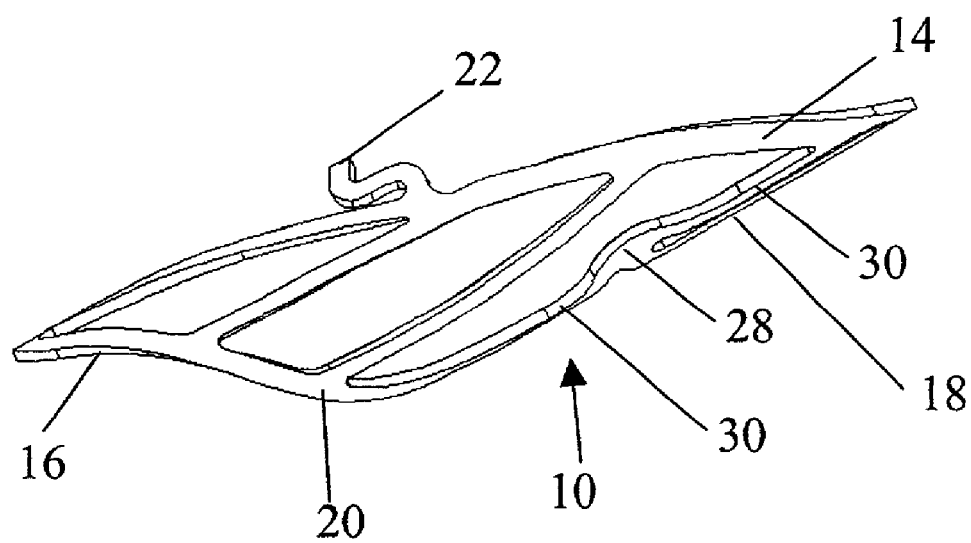
FIGS. 4a and 4b show side and perspective views of a non-formed connector blanks, which when formed represents the connector in FIGS. 3a and b.
Figure 4B:
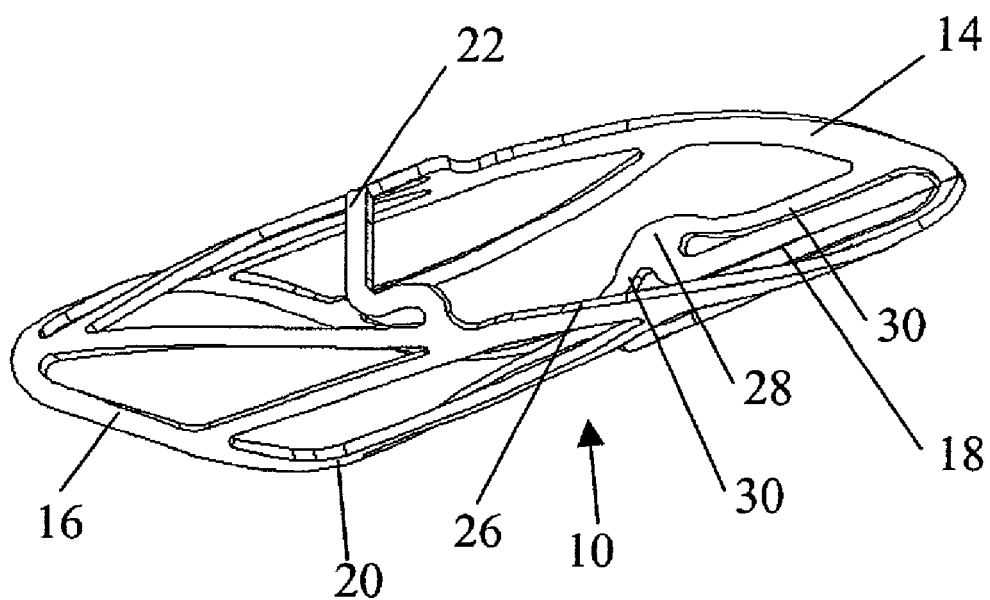
Figure 5:
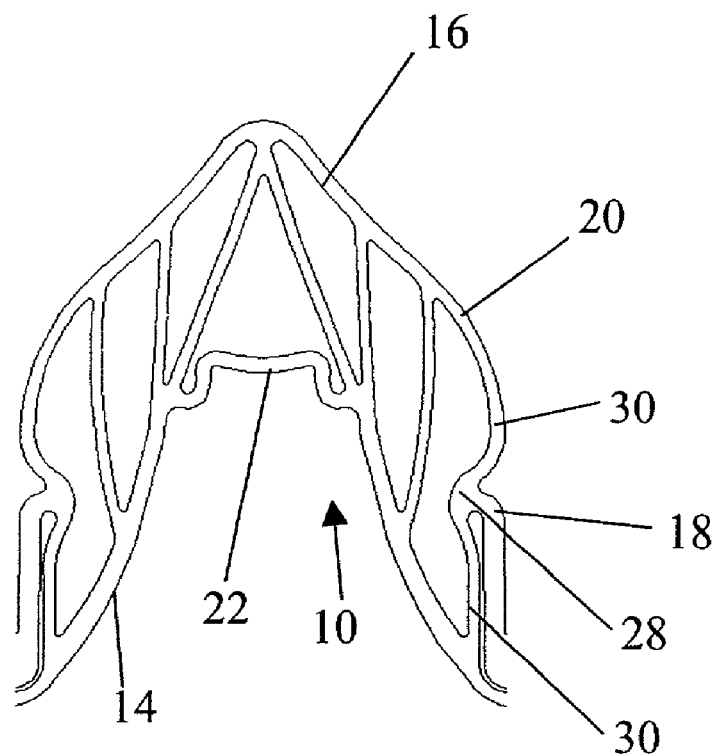
FIG. 5 shows a flattened view of the connector in FIGS. 4a and b.

This being said, FIGS. 5, 4a–4b, and 3a–3b show views of a connector fitting (10) at different stages of production being made from tubing. FIG. 5 shows the flattened profile of the tubing laser cutting to obtain the fitting blank. FIGS. 4a and 4b show the laser cut fitting blank. FIGS. 3a and 3b show the thermally formed fitting. The tube stock used to prepare distal connector fitting preferably has an outer diameter between 0.080 and 0.240 in (2 to 6 mm) and a wall thickness between 0.004 and 0.008 in (0.1 to 0.2 mm). Slightly larger diameter stock (or end product) will be used for each matching collar. The stock thickness for NiTi material used to form collars will typically have a wall thickness between about 0.004 in and about 0.008 in, and preferably between about 0.006 in and about 0.010 in. Especially, for fitting (10) where it is possible to use thin stock in view of strength requirements, this will be preferred in order to minimally obstruct blood flow past the fitting. Larger connector components will typically be made of thick stock to account for increased stiffness required of such configurations relative to smaller ones.

The invention has been described and specific examples or variations of the invention have been portrayed. The use of those specific examples is not intended to limit the invention in any way. In all, it is to be understood that each of the features described in connection with the various connector components and projections for forming the same may be mixed and matched to form any number of desirable combinations. Further, it is contemplated that additional details as to the use or other aspects of the system described herein may be drawn from the Abstract, Field of the Invention, Background of the Invention, Summary of the Invention, Brief Description of the Drawings, the Drawings themselves and Detailed Description and other background that is intended to form part of the present invention, including any of the patent applications cited above, each of which being incorporated by reference herein in its entirety for any purpose. Also, to the extent that there are variations of the invention which are within the spirit of the disclosure and are equivalent to features found in the claims, it is the intent that the claims cover those variations as well. All equivalents are considered to be within the scope of the claimed invention, even those which may not have been set forth herein merely for the sake of relative brevity. Finally, it is contemplated that any single feature or any combination of optional features of the inventive variations described herein may be specifically excluded from the invention claimed and be so-described as a negative limitation.

We claim:

1. An anastomosis connector system, comprising:
a fitting comprising a base adapted for attachment to a graft, a leading segment adapted for introduction into a host vessel, and a trailing segment comprising at least one lateral portion having a proximal end and a distal end, wherein the proximal end of the lateral portion is integrally attached along a torsional region which extends between the base and the leading segment,
wherein the trailing segment is deflectable about the torsional region from a first position to a second position such that at least the leading segment and the trailing segment can be advanced into the host vessel and wherein the trailing segment is adapted to return to the first position such that retraction from the host vessel is inhibited, and
wherein said fitting has a major axis extending from said leading segment to said trailing segment and has a minor axis transverse to said major axis, wherein a dimension of said fitting along said major axis is greater than a dimension of said fitting along the minor axis.

2. The system of claim 1 wherein the torsional region comprises at least a proximal torsional member and a distal torsional member, wherein the proximal torsional member extends between the lateral portion and the base and the distal torsional member extends between the lateral portion and the leading segment.

3. The system of claim 1 wherein the trailing segment is integrally formed with the base and the leading segment such that they form a continuous support member for placement along an interior surface of the host vessel.

4. The system of claim 1 wherein the fitting defines an angle between about 20° and about 70° between a distal end of the graft and a portion of the host vessel adjacent the graft.

5. The system of claim 4 wherein the fitting defines an angle of about 30° between a distal end of the graft and a portion of the host vessel adjacent the graft.

6. The system of claim 1 wherein the fitting further comprises lateral extensions between the leading segment and the trailing segment.

7. The system of claim 6 wherein the lateral extensions are formed by portions that are contiguous with the leading segment.

8. The system of claim 6 wherein the lateral extensions are adapted to be drawn inward upon deflecting the trailing segment about the torsional region.

9. The system of claim 1 wherein the fitting is adapted to be compressed to a reduced configuration.

10. The system of claim 1 wherein the trailing segment is deflected in the second position towards the leading segment.

11. The system of claim 1 wherein the trailing segment is deflected in the second position away from the leading segment.

12. The system of claim 1 wherein the fitting further comprises at least one tab adapted to secure the graft to the base.

13. The system of claim 1 further comprising a collar which is adapted to secure the graft to the host vessel between the fitting and the collar.

14. The system of claim 13 wherein the collar further comprises a collar tab adapted to interface with a complementary tab located on the fitting for securing the graft between the fitting and the collar.

15. The system of claim 14 wherein the collar further comprises at least one side spring member which extends from a heel portion of the collar to the collar tab.

16. The system of claim 15 wherein the side spring member is formed into a looped configuration.

17. The system of claim 13 wherein the collar further comprises at least one expansion spring member which is biased to compress the collar about the fitting.

18. The system of claim 17 wherein the expansion spring member has an undulating pattern when the collar is compressed about the fitting, and wherein the expansion spring member forms a straightened shape when the collar is in an expanded configuration.

19. The system of claim 13 wherein the collar further comprises a distal band member which extends around the graft from a heel portion and is adapted to urge the graft against the collar.

20. The system of claim 19 wherein the distal band member has a semicircular shape.

21. The system of claim 19 further comprising a looped member disposed along the distal band member at a toe portion which is in apposition to the heel portion.

22. The system of claim 13 wherein the collar comprises a split member.

23. The system of claim 13 wherein the collar comprises a biocompatible material selected from the group consisting of stainless steel, titanium and titanium alloys.

24. The system of claim 23 wherein the titanium alloy comprises NiTi.

25. The system of claim 13 wherein the collar further comprises a coating selected from the group consisting of biologically inert and biologically reactive materials.

26. The system of claim 13 wherein the collar comprises a wireform.

27. The system of claim 26 wherein the wireform is produced by a method selected from the group consisting of electron discharge machining, mechanical cutting, laser cutting, laser drilling, water-jet cutting, and chemically etching.

28. The system of claim 26 wherein the wireform is comprised of a singular integral structure.

29. The system of claim 26 wherein the wireform is produced from tubing stock or flat stock from which material is removed.

30. The system of claim 29 wherein the tubing stock or flat stock has a wall thickness between about 0.004 in and about 0.008 in.

31. The system of claim 1 wherein the fitting comprises a biocompatible material selected from the group consisting of stainless steel, titanium, and titanium alloy.

32. The system of claim 31, wherein the titanium alloy comprises NiTi.

33. The system of claim 1 wherein a superelastic effect returns the trailing segment from the second position to the first position.

34. The system of claim 1 wherein a thermoelastic or shape-memory effect returns the trailing segment from the second position to the first position.

35. The system of claim 1 further comprising an instrument adapted to hold the fitting for deployment by deflecting the trailing segment.

36. The system of claim 1 wherein the fitting further comprises a coating selected from the group consisting of biologically inert and biologically reactive materials.

37. The system of claim 1 wherein the fitting comprises a wireform.

38. The system of claim 37 wherein the wireform is produced by a method selected from the group consisting of electron discharge machining, mechanical cutting, laser cutting, laser drilling, water-jet cutting, and chemically etching.

39. The system of claim 37 wherein the wireform is comprised of a singular integral structure.

40. The system of claim 37 wherein the wireform is produced from tubing stock or flat stock from which material is removed.

41. The system of claim 40 wherein the tubing stock or flat stock has a wall thickness between about 0.004 in and about 0.008 in.

42. An anastomosis connector system, comprising:
   a fitting comprising a base adapted for attachment to a graft, a leading segment adapted for introduction into a host vessel, and a trailing segment comprising at least one lateral portion having a proximal end and a distal end, wherein the proximal end of the lateral portion is integrally attached along a torsional region which extends between the base and the leading segment; and
   a collar which is adapted to secure the graft to the host vessel between the fitting and the collar;
   wherein the trailing segment is deflectable about the torsional region from a first position to a second position such that at least the leading segment and the trailing segment can be advanced into the host vessel and wherein the trailing segment is adapted to return to the first position such that retraction from the host vessel is inhibited,
   wherein the torsional region comprises at least a proximal torsional member, which extends between the lateral portion and the base, and a distal torsional member, which extends between the lateral portion and the leading segment.

43. The system of claim 42 wherein the collar comprises a collar tab adapted to interface with a complementary tab located on the fitting for securing the graft between the fitting and the collar.

44. The system of claim 42 wherein the collar further comprises at least one expansion spring member which is biased to compress the collar about the fitting.

45. The system of claim 42 wherein the collar further comprises a distal band member which extends around the graft from a heel portion and is adapted to urge the graft against the collar.

* * * * *